United States Patent [19]

Mondabaugh et al.

[11] 4,178,359
[45] Dec. 11, 1979

[54] IMMUNOASSAY METHOD

[75] Inventors: Susan M. Mondabaugh, North Caldwell; Magdalena U. Gomez, Wayne, both of N.J.

[73] Assignee: Hoffmann-La Roche Inc., Nutley, N.J.

[21] Appl. No.: 886,849

[22] Filed: Mar. 15, 1978

Related U.S. Application Data

[63] Continuation-in-part of Ser. No. 731,237, Oct. 12, 1976, abandoned.

[51] Int. Cl.$^2$ .................... G01N 33/16; A61K 43/00
[52] U.S. Cl. ........................ 424/1; 23/230 B; 424/12; 435/7; 435/35
[58] Field of Search ................ 424/1, 1.5, 12; 23/230 B; 195/103.5 R

[56] References Cited

U.S. PATENT DOCUMENTS 3,974,269   8/1976   Maley ................................ 424/1.5

FOREIGN PATENT DOCUMENTS 1508104   4/1978   United Kingdom ................ 424/12

*Primary Examiner*—Leland A. Sebastian
*Assistant Examiner*—Christine M. Nucker
*Attorney, Agent, or Firm*—Jon S. Saxe; George M. Gould; Frank P. Hoffman

[57] ABSTRACT

An improved method for immunoassay for antibodies to microbial organisms is disclosed. The improvement involves the use of diluted anti-human IgG to produce a non-visible agglutinate of the microbial antigen-serum antibody cojugate. Such method provides for maximum label binding and thus maximum assay sensitivity compared to the previously employed conjugate precipitation method. The present improvement is particularly useful in a radioimmunoassay for detecting antibodies to *Neisseria gonorrhoeae* (N.g.) or rubella virus in sera.

10 Claims, No Drawings

IMMUNOASSAY METHOD

RELATED APPLICATIONS

This application is a continuation-in-part of copending application Ser. No. 731,237 filed Oct. 12, 1976, abandoned.

BACKGROUND OF THE INVENTION

One of the techniques for assaying for antibodies to microbial organisms involves forming a conjugate between the antibody and an antigen derived from the microbe such as, for example, from the cell wall thereof. The conjugate is precipitated from the test solution by the presence of an anti-antibody derived from a different mammalian species. By introducing a suitable label into the conjugate utilizing either a labelled antigen or a labelled anti-antibody, it is possible to determine the concentration of the antibody in the sample using a previously generated standard curve.

Thus, for example, detection of gonorrhea antibodies in human serum is described in U.S. Pat. No. 3,974,269. The method is based on the use of an antigen produced by the *Neisseria gonorrhoeae* organism whose isolation is described in further detail in U.S. Patent Application Ser. No. 385,863 filed Aug. 6, 1973.

In a specific embodiment of a radioimmunoassay described in U.S. Pat. No. 3,974,269, N.g. antibodies in serum are detected by a process comprising:

A. Adding anti-human IgG to the serum to be tested in a buffer aqueous medium;

B. Thereafter adding a heat labile antigen labelled with a radioactive element;

C. Incubating the resulting mixture at from about 4° to 45° C. for from about 24 to 2 hours at a pH of from about 6.5 to 8.5 to form an antigen-antibody conjugate when antibodies are present in the serum; and D. Determining the level of radioactivity as a measure of the presence of the antigen-antibody conjugate.

The precipitated conjugate is separated from the solution by either filtration or centrifugation. In accordance with the prior knowledge and practice in the art, the amount of anti-human IgG used in relation to the amount of serum in step A is adjusted to maximize precipitation. The assumption has always been that maximum precipitation is equivalent to maximum radioactivity yield. To this end the ratio of anti-human IgG antibody to serum sample volumes is adjusted to substantially more than 1/1, usually a ratio of 6/1 is used.

Several problems remain before such techniques can be utilized as the basis for mass screening tests. One major problem is the fact that the positive cut off level is three standard deviations above the mean of a group of negative sera even at maximum sensitivity. Thus, the test would pick up positive sera having relatively high antibody titers but would not accurately pick up sera having weak or borderline concentrations of antibody which still represent subjects with positive infections of the microbe agents in question. Moreover, in order to reach this level of sensitivity it is critically necessary to add the reagents in specific order, that is the anti-human IgG is added to the buffered test serum followed by addition of the labelled antigen. Use of the normal order wherein the antigen is added to the serum followed by the anti-human IgG results in a test which is indicated to be of insufficient sensitivity to distinguish between positive and negative sera with a useful degree of confidence.

A solid-phase radioimmunoassay for rubella virus is described by Kalimo et al., J. Clin. Microbiol. 4, No. 2, 117 (1976). This assay employs rubella virus adsorbed onto polystyrene balls.

DESCRIPTION OF THE INVENTION

The present invention relates to an improved method for immunoassay for antibodies to microbial organisms in mammalian serum, particularly organisms having molecular weights of greater than about 1,000,000 daltons. In particular, the present improvement relates to immunoassays for said antibodies wherein a second antibody is added to the immunological reaction mixture in order to assist in the efficient precipitation of the antigen-microbial specific antibody conjugate from the medium. This second antibody is elicited from a mammalian species other than the test species and is specific to the IgG fraction of the test species, i.e., an anti-IgG antibody.

As is indicated above, it is conventional in this art to utilize an excess volume ratio of anti-IgG serum compared to test serum when conducting such assay. This is due to the desire to maximize precipitation which it is believed will be equivalent to maximizing the amount of labelled antigen or antibody recovered. It is the efficiency of such recovery that influences to a great degree the sensitivity of the procedure.

It has now been discovered that, contrary to the established beliefs in the art, maximum yield of label is not obtained by maximizing the precipitation of the antibody-antigen conjugate. Rather, quite surprisingly, maximum label recovery is observed to occur in such method when the volume ratio of anti-antibody to serum sample is adjusted so as to produce a non-visible agglutination of the conjugate. The ratio needed to produce such agglutination is substantially below that needed for precipitation. While the precise volume ratio ranges utilized to effect agglutination will vary depending on the identity of the specific reagents employed in the assay, they will ordinarily be lower than 1/1 and generally will be between 1/2 and 1/250. Thus, for example, in an immunoassay for gonorrhea antibody the volume ratio is preferably from 1/5 to 1/250, while for rubella virus antibody the volume ratio is about 1/80.

Since volumes of reagents used in immunoassays are relatively small, for example, in radioimmunoassays they may be in the order of about 5 $\mu$l for the serum sample, it is more convenient to dilute the anti-antibody and add equal volumes of this diluted reagent to the test serum. Dilutions can be accomplished using either serum from the mammalian species in which the anti-antibody was elicited or else phosphate buffered saline (PBS) as diluent.

The improved method of the instant invention can be used in immunoassays directed towards detection of antibodies present in mammalian blood serum which are directed to microbial organisms. Thus, the instant method can be utilized as a diagnostic screen in detecting infection by such microbial organisms. Among the microbial organisms to which the method can be directed include, without limitation, viruses such as rubella; bacteria such as *Neisseria gonorrhoeae, Neisseria meningitidis, Treponema pallidum,* and *Streptococcus pyogenes;* fungi such as *Histoplasma capsalatum;* yeast such as *Candida albicans;* and parasites such as *Trichomonas vaginalis.*

The formation of the first antibody-antigen-second antibody conjugate agglutinate can be detected by a number of methods available in the art. Either the antigen derived from the subject virus or microbe or the second antibody can be labelled in a manner known per se. It is also possible to employ subunits of the virus such as the hemagglutinating subunit of rubella virus as the substrate. Such labels may include a detectable radioactive element such as $^3$H, $^{14}$C, $^{125}$I and the like; an enzyme such as described in U.S. Pat. No. 3,817,837; an electron spin resonance group such as described in U.S. Pat. Nos. 3,453,288, 3,481,952, 3,507,876 and 3,690,834; a fluorophore such as fluorescamine, MDPF, fluorescein, rhodamine, auramine and the like; or chromophores.

The second or anti-antibody employed in the practice of the invention is elicited from a mammalian species different than the species whose serum is to be tested for the viral or microbial antibody. Thus, for example, if human blood serum is utilized as the test serum then anti-human IgG derived from sheep or goat serum can be utilized. Such materials are available as articles of commerce.

In a preferred embodiment of the invention detection of the agglutinate is accomplished by the use of a labelled antigen, most preferably an $^{125}$I-labelled antigen. Such a label can be introduced by utilizing procedures known in the art, such as, for example, as described by Syvanen et al., J. Biol. Chem., 248, 3762 (1973) or the modified procedure described in U.S. Pat. No. 3,974,269. $^{125}$I-labelled second antibody can be prepared by a modification of the Hunter and Greenwood procedure such as described by Kalimo et al., J. Clin. Microbiol., 4, No. 2, 117 (1976).

The subject conjugate is formed by a reaction which takes place in an aqueous medium at a pH of from about 6.5 to 8.5 during a period of from about 2 to 24 hours at a temperature of from about 4°–45° C. Reaction is effected by mixing serum under test with aqueous buffer, labelled antigen and anti-antibody. The order of addition is not critical.

In a typical procedure for the detection of microbial antibodies by radioimmunoassay a reaction mixture comprising 0.1 ml. of phosphate buffered saline (pH 7.2); 5 μl of test serum; 5 μl of anti-antibody diluted 1/2 to 1/250 with buffer or normal serum; and 50 μl of $^{125}$I-labelled antigen (8,000 cpm at 70% counting efficiency) is prepared. The reaction mixture is incubated at 4° C. overnight (about 16 hours) and at the end of this period 0.5 ml. of PBS is added. The agglutinated material obtained is filtered through a 2.4 cm Whatman GF/C filter using a Millipore manifold filter apparatus. Although the agglutinated conjugate is not visible it is retained by the filter in the above procedure. The filter is then washed well with distilled water and the label detected by counting the radioactivity.

In order to minimize nonspecific binding of antigen, it is desirable to prewash the filter. The preferred prewash medium is bovine serum albumin although other reagents such as human serum immunoglobulin, ovalbumin and hemoglobin may also be employed. The preferred prewash is with 0.5 ml. of a solution containing 2% by weight fraction V BSA together with a chelating agent such as 0.01 M ethylenediamino tetraacetic acid (EDTA).

EXAMPLE 1 i. Method

In a typical procedure for the detection of Gc antibodies, the following reagents are added and mixed well: 0.1 ml. of phosphate buffered saline, pH 7.2; 5 μl of patient serum, 5 μl of a 1/16 dilution of goat antihuman IgG in normal goat serum and 50 μl of $^{125}$I-labelled Gc-antigen (8000 cpm). The order of addition of reagents is not important. After an overnight incubation at 4° C., 0.50 ml. of PBS are added to provide a volume large enough to facilitate handling. The antigen-antibody agglutinate is filtered through a 2.4 cm. Whatman GF/C filter using a Millipore Manifold (the filters must be presoaked with a bovine serum albumin solution). After thoroughly washing the filter, it is dried by gentle vacuum and counted in a gamma scintillation counter.

ii. Comparison of present methodology with that of U.S. Pat. No. 3,974,269

A series of 5 Gc culture negative sera (1–5) and 12 Gc culture positive sera (6–17) were run employing the present methodology and also that of U.S. Pat. No. 3,974,269. As can be seen in Table I, all of the positive sera are detected by the present assay yet four out of twelve sera or 33% are missed by the methodology of U.S. Pat. No. 3,974,269. The sensitivity of the method of the present invention is therefore superior to that of the published one. It is also important to notice that the binding of the lable is also much greater. The ratio of the counts obtained by the present method to the counts obtained according to U.S. Pat. No. 3,974,269 is on the average 3.25 (range 1.15–5.59).

Table I

| Sample | Culture Results | Patent 3,974,269 (cpm) | Patent 3,974,269 Results | Present Method (cpm) | Present Method Results | Ratio = Present cpm / Patent cpm |
| --- | --- | --- | --- | --- | --- | --- |
| 1 | — | 165 | — | 123 | — | |
| 2 | — | 137 | — | 98 | — | |
| 3 | — | 129 | — | 120 | — | |
| 4 | — | 97 | — | 204 | — | |
| 5 | — | 154 | — | 207 | — | |
| 6 | + | 204 | — | 1000 | + | 4.90 |
| 7 | + | 97 | — | 524 | + | 5.40 |
| 8 | + | 225 | — | 788 | + | 3.50 |
| 9 | + | 111 | — | 817 | + | 3.60 |
| 10 | + | 575 | + | 662 | + | 1.15 |
| 11 | + | 444 | + | 915 | + | 2.06 |
| 12 | + | 534 | + | 789 | + | 1.47 |
| 13 | + | 1783 | + | 2319 | + | 1.30 |
| 14 | + | 698 | + | 2266 | + | 3.20 |
| 15 | + | 394 | + | 2206 | + | 5.59 |
| 16 | + | 571 | + | 2052 | + | 3.59 |

Table I-continued

| Sample | Culture Results | Patent 3,974,269 (cpm) | Patent 3,974,269 Results | Present Method (cpm) | Present Method Results | Ratio = Present cpm / Patent cpm |
| --- | --- | --- | --- | --- | --- | --- |
| 17 | + | 1333 | + | 2542 | + | 1.90 |

EXAMPLE 2

Growth of Rubella Virus in Vero Cells

A continuous line of African green monkey kidney cells (Vero) was grown to confluency at 37° C. in glass roller bottles (500 mm length) using the following medium: Minimal Essential Medium (Eagle) with Earle's salts and containing 3.0 ml./100 ml. of 7.5% NaHCO$_3$, 10 ml./100 ml. of heat-inactivated new-born bovine serum, 1 ml./100 ml. of 200 mM glutamine and penicillin-streptomycin (100 units/ml.-100 µg/ml.).

Infection of Vero Cells with Rubella Virus

Tissue culture medium was removed from roller bottles containing confluent monolayers of Vero cells and each monolayer was washed once with phosphate buffered saline (without calcium and magnesium) pH 7.2. Stock preparations of rubella virus (strains M-33 or Gilchrist) were diluted approximately 1-50 or 1-100 in Minimal Essential Medium (Eagle) prepared as previously described with the exception that new-born bovine serum was omitted and a serum substitute consisting of 20 ng/ml. of the synthetic tripeptide glycyl-L-histidyl-L-lysine acetate were added. Thirty ml. of the diluted virus inoculum were added to each roller bottle and virus adsorption was for 1 hour at 24° C. at 2 rpm. At the end of the adsorption period, 70 ml. of Minimal Essential Medium (Eagle) containing NaHCO$_3$, glutamine, penicillin-streptomycin and the synthetic tripeptide glycyl-L-histidyl-L-lysine (as described above) were added to each rubella virus-infected monolayer. Incubation was continued at 34° C. at 1 rpm.

Concentration of Rubella Virus

Beginning on the third day after visus infection, the tissue culture fluids were removed from each roller bottle of rubella-infected Vero cells and each bottle was refed with 100 ml. of the serum free Minimal Essential Medium (Eagle) previously described. Harvesting of supernatant fluid was continued daily for an additional 8-10 days after virus infection.

Pooled supernatant fluids were clarified of cell debris by centrifugation at 5,000 rpm for 30 minutes at 4° C. Rubella virus in clarified supernatant fluids was then concentrated approximately one hundred-fold using an Amicon DC-2 hollow fiber concentrator equipped with a 10,000 molecular weight cut-off hollow fiber filter. Final concentration of virus was made in phosphate buffered saline, without calcium and magnesium, at pH 8.0. Concentrated virus was stored at −70° C.

Iodination of Rubella Virus

The following components were added to a 3.0 ml. V-vial:
1. 100 µl rubella virus (about 150 µg/ml. of protein);
2. 200 µl 0.5 M potassium phosphate, pH 7.5;
3. 20 µl $^{125}$I (5 mCi);
4. 20 µl Chloramine-T (0.5 mg./ml.).

After incubation for 1 minute at room temperature with gentle shaking, 5. 500 µl sodium bisulfite (0.1 mg./ml.) were added to the V-vial and incubation for 30 seconds at room temperature with gentle shaking was completed before addition of
6. 200 µl KI (1 mg./ml.);
7. 40 µl bovine serum albumin (10%), Fraction V.

Column Chromatography of Iodinated Rubella Virus

Iodinated rubella virus was applied to a 1×30 cm column of agarose beads (BioGel® A-1.5 m) previously equilibrated with 0.05 M potassium phosphate, pH 7.0. Fifty fractions (1.0 ml.) were collected and the CPM of a 20 µl aliquot from each fraction was determined in a gamma scintillation counter.

Appropriate tubes comprising the first peak of radioactivity recovered from the agarose-bead column were pooled and the cpm was adjusted to 50,000/50 µl with 1% bovine serum albumin (BSA) containing 0.02 M ethylenediaminetetraacetic acid (EDTA).

Determining Optimum Dilutiion for Second Antibody (Goat anti-Human IgG

1. Candidate human serum (hereinafter referred to as the first antibody) was diluted 1-10 in phosphate buffered saline containing 0.1% sodium azide and was used without further treatment. This serum when treated and tested by conventional techniques in a hemagglutination inhibition (HI) test exhibited a titer in the range of 1/80 to 1/160.

2. Goat anti-human IgG (hereinafter referred to as the second antibody) was diluted from 1-10 through 1-2560 in normal goat serum (NGS).

3. Triplicate glass test tubes, 12×75 mm, received the following:
   a. 100 µl PBS, pH 7.2;
   b. 5 µl first antibody (high rubella HI titer human sera);
   c. 10 µl second antibody (goat anti-human IgG diluted 1-10 to 1-2560 in NGS);
   d. 50 µl of $^{125}$I-labelled rubella virus (hereinafter referred to as the antigen) adjusted to 50,000 CPM.

4. Glass tubes were shaken vigorously and incubated at room temperature for 4 hours.

5. Glass microfiber paper filters, 2.4 cm, (Whatman GF/C) were placed in the individual wells of a vacuum filtration system (Millipore 3025 sampling manifold). To each filter were added 500 µl of 2% BSA-0.01 M EDTA and this solution was removed by vacuum after 5 minutes.

6. The test tubes described in (3) above which contained first antibody, second antibody and antigen, received an additional 500 µl of PBS. The total volume of each tube was added to individual glass microfiber paper filters treated as described in (5) above. Fluids were removed by vacuum filtration and each filter was washed 3 times with distilled H$_2$O.

7. After the last rinse of the filters with distilled H$_2$O, each filter was removed and placed in a 12×75 mm plastic tube. The CPM/tube was determined in a gamma scintillation counter with counting time equal to 1 minute.

The results obtained in a titration of the second antibody against a constant dilution of the first antibody are shown in Table 2.

Table 2

Titration of Human Serum (First Antibody) Against Goat Anti-Human IgG (Second Antibody) Diluted from 1-10 to 1-2560 In Normal Goat Serum

| First Antibody[1] | Dilution of Goat Anti-Human IgG[2] | Average CPM |
|---|---|---|
| Rubella HI High Titer Human Serum | 1-10 | 1524 |
| | 1-20 | 1660 |
| | 1-40 | 1788 |
| | 1-80 | 1996 |
| | 1-160 | 1607 |
| | 1-320 | 1237 |
| | 1-640 | 1096 |
| | 1-1280 | 1101 |
| | 1-2560 | 883 |

[1] First antibody diluted 1-10 in PBS
[2] Second antibody diluted in normal goat serum From the results shown in Table 2 it can be seen that the highest average CPM was obtained with a 1-80 dilution of the second antibody against a constant dilution (1-10) of the first antibody.

Evaluation of High, Low and Negative Rubella HI Titer Human Sera by a Radioimmunoassay Procedure 1. First antibody was used having a high titer (80-160) and a low titer (10-20), said titer levels being determined by HI test as before. Additionally, a negative serum having a titer below 10 was used.

2. Goat anti-human IgG was used as second antibody diluted to 1/80 with NGS.

3. Triplicate glass test tubes, 12×75 mm, received the following:
   a. 100 μl PBS, pH 7.2;
   b. 5 μl first antibody (high, low or negative rubella HI titer human sera);
   c. 10 μl second antibody (goat anti-human IgG diluted 1/80 in NGS);
   d. 50 μl of $^{125}$I-labelled antigen adjusted to 50,000 CPM.

4. Glass tubes were shaken vigorously and incubated at room temperature for four hours.

5. Test specimens were added to glass microfiber paper filters and radioactivity (CPM) was determined as previously described in paragraphs (5), (6) and (7) of the section *Determining Optimum Dilution for Second Antibody (Goat anti-human IgG)*.

6. The results, expressed as average CPM, obtained in such a radioimmunoassay procedure as described herein with human sera of known HI titer are shown in Table 3.

Table 3

Use of Radioimmunoassay Procedure to Detect Antibody to Rubbela Virus in Human Sera of Known Hemagglutination-Inhibition Titer

| HI Titer of Human Serum[1] | Average CPM |
|---|---|
| High (80-160) | 3036 |
| Low (10-20) | 1857 |
| Negative (<10) | 1584 |

[1] Diluted 1-10 in PBS.

From the results shown in Table 3 it can be seen that the average CPM was proportional to the HI titer of the test serum. For example, a high titer serum (HI titer 80-160) had an average CPM of 3036, a low titer serum (HI titer of 10-20) had an average CPM of 1857 and a negative titer serum (HI titer <10) had an average CPM of 1584. By constructing 95% confidence intervals the following standards were obtained: (1) for a test serum to have a HI titer of 80-160 the CPM must be at least 2378 and (2) for a test serum to have a HI titer of 10-20 the CPM must be at least 1678. Any test serum with a CPM less than 1678 would be considered to have a HI titer of less than 10 and therefore would be considered a negative.

Stability of $^{125}$I-Labelled Rubella Virus

Following iodination of rubella virus, the radioactivity was adjusted to 50,000 CPM/50 μl by dilution of the antigen in 1% BSA containing 0.02 M EDTA. The antigen was stored at 4° C. and performed satisfactorily for a period of 4 weeks.

We claim:

1. In an immunoassay for determining the presence of microbial antibodies in mammalian serum which comprises the steps of:
   A. Providing a reaction mixture comprising a buffered aqueous medium; serum to be sampled; antigen derived from said virus or microbes and anti-antibody to the serum to be tested, said antigen or anti-antibody bearing a detectable label;
   B. Incubating said reaction mixture at from about 4° to 45° C. for from about 24 to 2 hours at a pH of from about 6.5 to 8.5 to form an antigen-antibody conjugate when said microbial antibody is present in said serum sample; and
   C. Determining the level of said label as a measure of the presence of said antigen-antibody conjugate;
   the improvement which comprises adjusting the volume ratio of anti-antibody to serum sample to a value sufficient to form an agglutinate but less than required to effectuate precipitation of the antigen-antibody conjugate.

2. The improved immunoassay of claim 1 wherein the volume ratio of anti-antibody to serum sample is in the range of between 1/2 and 1/250.

3. The improved immunoassay of claim 2 wherein equal volumes of anti-antibody and serum sample are used, said desired volume ratio being achieved by dilution of said anti-antibody.

4. The improved immunoassay of claim 3 wherein said label is a radioactive element and said immunoassay is a radioimmunoassay.

5. The improved immunoassay of claim 4 wherein said microbe is *Neisseria gonorrhoeae*; said mammalian serum is human serum; said detectable label is antigen from *Neisseria gonorrhoeae* labelled with $^{125}$I; said anti-antibody is anti-human IgG; and said volume ratio of anti-antibody to serum sample is in the range of from about 1/5 to about 1/250.

6. The improved immunoassay of claim 5 wherein the incubation is carried out at about 4° C. for about 16 hours at a pH of about 7.2.

7. The improved radioimmunoassay of claim 3 wherein said diluent is selected from aqueous buffer or normal mammalian serum.

8. The improved radioimmunoassay of claim 4 wherein the agglutinated conjugate is separated from the reaction mixture by filtration and said filter is then washed and counted for radioactivity to determine the amount of conjugate collected which is proportional to the microbial antibody level in the serum sample.

9. The improved immunoassay of claim 4 wherein said microbe is a virus.

10. The assay of claim 9 wherein said virus is rubella virus; said mammalian serum is human serum; said detectable label is purified rubella virus labelled with $^{125}I$; said anti-antibody is anti-human IgG; and said volume ratio of anti-antibody to serum sample is about 1/80.

* * * * *